United States Patent [19]

Murata et al.

[11] Patent Number: 5,330,668

[45] Date of Patent: Jul. 19, 1994

[54] ORGANIC FERROMAGNETIC SUBSTANCE AND PROCESS FOR PRODUCING SAME

[75] Inventors: Kazuhisa Murata, Tsukuba; Akio Matsuda, Kashiwa; Takashi Masuda, Abiko, all of Japan

[73] Assignee: Director-General of Agency of Industrial Science & Technology, Japan

[21] Appl. No.: 843,181

[22] Filed: Feb. 28, 1992

[30] Foreign Application Priority Data

Jun. 25, 1991 [JP] Japan ................... 3-180213

[51] Int. Cl.⁵ ................... H01F 1/00; C07G 17/00
[52] U.S. Cl. ................... 252/62.51; 252/500; 528/481
[58] Field of Search ................... 252/62.51, 62.54, 500; 528/481

[56] References Cited

U.S. PATENT DOCUMENTS 4,626,588  12/1986  Murase et al. ................... 528/481
5,015,699   5/1991  Cotts et al. ................... 252/62.54
5,135,673   8/1992  Murata et al. ................... 252/62.54

FOREIGN PATENT DOCUMENTS 414537    2/1991  European Pat. Off. .
2-296710 12/1990  Japan .

OTHER PUBLICATIONS

Patent Abstracts of Japan, vol. 015, No. 072, Feb. 20, 1991.

*Primary Examiner*—Prince Willis, Jr.
*Assistant Examiner*—Alan D. Diamond
*Attorney, Agent, or Firm*—Lorusso & Loud

[57] ABSTRACT

An organic ferromagnetic substance including an amorphous carbonaceous substance in mid course of graphitization prepared from an organic compound having a hydrogen/carbon ratio of 1.7 or more and a process for producing same are disclosed. This organic ferromagnetic substance is stable and easy to produce, and has a high saturation magnetization and is advantageous as an industrial product such as a toner for copiers utilizing its light weight and high saturation magnetization.

3 Claims, No Drawings

ORGANIC FERROMAGNETIC SUBSTANCE AND PROCESS FOR PRODUCING SAME

BACKGROUND OF THE INVENTION

This invention relates to an organic ferromagnetic substance and a process for producing same.

As metal-free organic ferromagnetic substances, there have so far been reported (i) diacetylene having a nitroxy radical in the 1,4-position thereof, (ii) polymers synthesized from pyrene and benzaldehyde, (iii) triaminobenzene polymers and (iv) indigo polymers. These conventional organic ferromagnetic substances, however, have the defects that they have a low saturation magnetization (about 0.5 emu/g or less) and require many steps for their synthesis.

SUMMARY OF THE INVENTION

It is an object of the present invention to provide an organic ferromagnetic substance which is easy to produce, which has an excellent stability and which shows a high saturation magnetization.

Another object of the present invention is to provide a process for producing the organic ferromagnetic substance.

These objects can be attained by a hydrogen-containing carbonaceous substance produced from a specific organic compound.

In accordance with one aspect of the present invention, there is provided an organic ferromagnetic substance comprising a carbonaceous substance in mid course of graphitization which is produced from an organic compound having a hydrogen-to-carbon ratio of 1.7 or more and which contains 1–50 hydrogen atoms per 100 carbon atoms.

In accordance with another aspect of the present invention, there is provided a process for producing an organic ferromagnetic substance comprising a carbonaceous substance in mid course of graphitization which is produced from an organic compound having a hydrogen-to-carbon ratio of 1.7 or more and which contains 1–50 hydrogen atoms per 100 carbon atoms by heating at least one organic compound selected from among those compounds which have a hydrogen-to-carbon ratio of 1.7 or more to a temperature of 500° C. or higher in a vacuum or inert gas.

Other objects, features and advantages of the present invention will become apparent from the detailed description of the preferred embodiments of the invention to follow.

DETAILED DESCRIPTION OF THE PREFERRED EMBODIMENTS OF THE INVENTION

The starting organic compounds are described in detail below.

The organic compounds to be used in the present invention are those which have a hydrogen-to-carbon ratio of 1.7 or more. Such compounds have conventionally been known.

A first type of the organic compounds to be preferably used in the present invention include aliphatic hydrocarbons and alicyclic hydrocarbons. These compounds are exemplified by those which are represented by the following general formulae (I) and (II). The organic compounds may be used alone or as a mixture thereof.

$$R_1\text{-}(CH_2)_{n_1}\text{-}R_2 \quad (I)$$

$$(II)$$

In the above general formulae, $R_1$–$R_3$ are the same or different and each stands for a hydrogen atom, an alkyl group, a trialkylmethyl group, an alkoxy group, a hydroxy group, a halogen atom or an amino group, $n_1$ represents an integer of 0, 1 or more and $n_2$ represents an integer of 2 or more. Specific examples of the compounds represented by the general formula (I) include pentane, octane, dodecane, dodecanol, dimethylpropane, dimethylbutane, diethyl ether, ethylenediamine, propanediamine, propyl chloride and tricyclohexylmethanol. Specific examples of the compounds represented by the general formula (II) include cyclohexane, methylcyclohexane, cyclohexanol, chlorocyclohexane, cyclohexylamine, cyclododecane and cyclopentadecane.

A second type of the organic compounds preferably used in the present invention are aza compounds. Examples thereof are chained or cyclic tetraza compounds represented by the following general formula (III) or (IV):

$$R_4R_5N\text{-}(CH_2)_{n_3}\text{-}N\text{-}(CH_2)_{n_4}\text{-}N\text{-}(CH_2)_{n_6}\text{-}NR_8R_9 \quad (III)$$

$$(IV)$$

In the above general formulae, $R_4$–$R_{14}$ are the same or different and each represents a hydrogen atom or an alkyl group, and $n_3$–$n_9$ each represents an integer of 1 or more. Specific examples of the compounds represented by the general formula (III) include 1,4,8,11-tetrazaundecane, 1,5,8,12-tetrazadodecane and 1,5,9,13-tetrazatridecane. Specific examples of the compounds represented by the general formula (IV) include 1,4,8,11-tetrazacyclotetradecane and 1,4,8,12-tetrazacyclopentadecane.

A third type of the organic compounds are crown compounds. Typical examples thereof are represented by the following general formulae (V) and (VI):

$$(V)$$

-continued

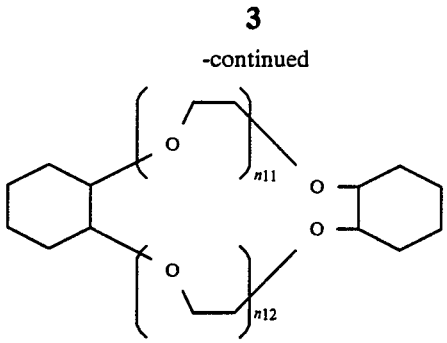
(VI)

In the above general formulae, $n_{10}$–$n_{12}$ each represents an integer of 1 or more, preferably 4–8. Specific examples of the compounds represented by the general formula (V) include 15-crown-5,18-crown-6, etc. Specific examples of the compounds represented by the general formula (VI) include cyclohexano-18-crown-6 and dicyclohexano-24-crown-8.

A fourth type of the organic compounds are amine compounds represented by the following general formula (VII):

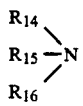
(VII)

wherein $R_{14}$–$R_{16}$ are the same or different and each stands for a hydrogen atom, an alkyl group, an alkoxy group or a hydroxy group.

The fifth type of the organic compounds are those which are represented by the following general formula (VIII):

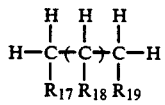
(VIII)

wherein $R_{17}$–$R_{19}$ are the same or different and each stands for a hydrogen atom, an alkyl group, an alkoxy group, a hydroxy group or an amino group.

The carbonaceous compounds of the present invention are produced by subjecting at least one compound selected from among those compounds which have a hydrogen-to-carbon ratio of 1.7 or more to a heat treatment at a temperature above 500° C., preferably 900°–1100° C., for 0.1–10 hours, preferably 0.3–2 hours, under vacuum or in the presence of an inert gas (e.g., an argon gas or a nitrogen gas). The upper limit of the heating temperature is about 3000° C.

In order to obtain a ferromagnetic amorphous carbonaceous substance by thermal carbonization of a specific organic compound according to the process of the present invention, it is necassary to control the heating condition so that there results a carbonaceous substance in mid course of graphitization containing hydrogen atoms. The mumber of hydrogen atoms in the carbonaceous substance is 1–50 per 100 carbon atoms.

According to a result of the powder X-ray diffraction analysis, a diffraction line (002) showing absorption of carbon usually detected in the vicinity of $2\theta=25°$ with graphite is not clearly detected. Laser-Raman analysis also does not show an absorption at 1580 cm$^{-1}$ which is specific to graphite. Thus, both analyses show that the carbonaceous substance is an amorphous substance in mid course of graphitization.

The present invention will now be illustrated in more detail by way of examples and comparative examples.

EXAMPLE 1

0.5 g of cyclododecane (hydrogen/carbon=2) was placed in a quartz reaction tube at the left end thereof and, after outgassing the tube under vacuum for about 3 hours, the right end of the tube was heated to 950° C. After the heated end became a reaction temperature, cyclododecane at the left end was heated to evaporate. The evaporated cyclododecane was guided to the heated right end of the tube. After completion of the reaction at 950° C. for 1 hour, the tube was cooled, and an amorphous carbonaceous product adhering to the reaction tube surface was taken out (about 0.04 g). At least part of the thus-obtained substance showed the property of being attracted by a permanent magnet (6000 gausses). This attracted portion (about 0.01 g) showed on the measurement of coercive force Hc and saturation magnetization Imax at ordinary temperature, an Hc of 102 Oe and an Imax of 1.21 emu/g, respectively. Elementary analysis of the carbonaceous substance revealed that the substance had a hydrogen-to-carbon ratio (H/C) of 0.305. In the powder X-ray diffraction analysis, this carbonaceous substance did not show a clear diffraction line of carbon (002) in the vicinity of $2\theta=25°$ which is observed with ordinary graphite, thus the carbonaceous substance being shown to be an amorphous substance.

EXAMPLES 2–12

The same reaction as in Example 1 was conducted except for changing the organic compound. Portions of the products attracted by a permanent magnet were measured as in Example 1 to obtain results as shown in Table 1.

COMPARATIVE EXAMPLES 1–2

The same reaction as in Example 1 was conducted except for changing cyclododecane by 0.5 g of pyrene (hydrogen/carbon=0.625) or 0.5 g of tetrahydrocarbazole (hydrogen/carbon=1,083). The thus-obtained carbonaceous substances showed considerably low saturation magnetization values as shown in Table 1.

TABLE 1

| | Organic Compound (H/C ratio) | Coercive Force (Oe) | Saturation Magnetization Imax (emu/g) |
|---|---|---|---|
| Example 2 | Cyclododecanol (2.0) | 91 | 0.532 |
| Example 3 | Cyclopentadecane (2.0) | 92 | 0.503 |
| Example 4 | n-Hexane (2.33) | 87 | 1.08 |
| Example 5 | Diethylamine (2.75) | 96 | 6.69 |
| Example 6 | Triethylamine (2.5) | 102 | 2.63 |
| Example 7 | Tricyclohexyl methanol (1.79) | 109 | 0.891 |
| Example 8 | 1,4,8,11-Tetrazacyclotetradecane (2.4) | 122 | 1.63 |
| Example 9 | 1.5.8.12-tetrazadodecane (2.75) | 112 | 1.92 |
| Example 10 | Dicyclohexano-18-crown-6 (1.80) | 115 | 1.28 |
| Example 11 | Di-n-propylamine (2.5) | 96 | 7.85 |
| Example 12 | 1,2-Propanediamine (3.33) | 120 | 9.37 |
| Comparative Example 1 | Pyrene (0.625) | 99 | 0.181 |

TABLE 1-continued

|  | Organic Compound (H/C ratio) | Coercive Force (Oe) | Saturation Magnetization Imax (emu/g) |
|---|---|---|---|
| Comparative Example 2 | Tetrahydrocarbazole (1.083) | 76 | 0.21 |

The organic ferromagnetic substance comprising the amorphous carbonaceous substnce in accordance with the present invention produced from a specific organic compound is advantageously used as an industrial product such as a toner of copiers and can find wide applications utilizing its ferromagnetic properties.

The invention may be embodied in other specific forms without departing from the spirit or essential characteristics thereof. The present embodiments are therefore to be condidered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. An organic ferromagnetic substance which comprises an amorphous carbonaceous substance in mid course of graphitization produced from an organic compound selected from the group consisting of:
   I. aza compounds selected from the group consisting of 1,4,8,11-tetrazaundecane, 1,5,8,12-tetrazadodecane, 1,5,9,13-tetrazatridecane, 1,4,8,11-tetrazacyclotetradecane and 1,4,8,12-tetrazacyclopentadecane;
   II. crown compounds represented by the following general formula (V) and (VI):

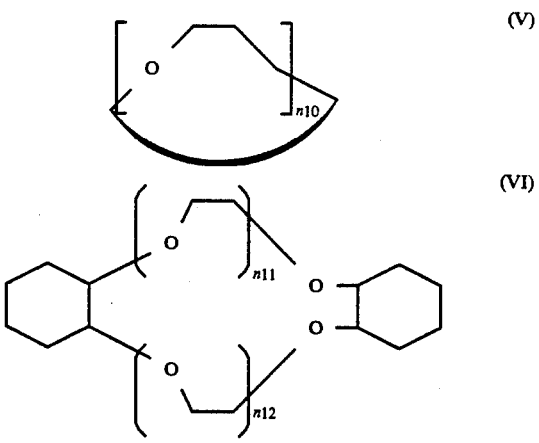

wherein $n_{10}$–$n_{12}$ each represent an integer of 1 to 8; and
   III. alkylamines,
   said organic compound having a hydrogen-to-carbon ratio of 1.7 or more and said carbonaceous substance having 1–50 hydrogen atoms per 100 carbon atoms.

2. An organic ferromagnetic substance as set forth in claim 1, wherein said organic compound is an alkylamine.

3. An organic ferromagnetic substance as set forth in claim 2, wherein said alkylamine is represented by the following general formula (VII):

wherein $R_{14}$–$R_{16}$ are the same or different and each stands for a hydrogen atom, an alkyl group, an alkoxy group or a hydroxy group.

* * * * *

UNITED STATES PATENT AND TRADEMARK OFFICE
CERTIFICATE OF CORRECTION

PATENT NO.  : 5,330,668
DATED       : July 19, 1994
INVENTOR(S) : MURATA et al

It is certified that error appears in the above-indentified patent and that said Letters Patent is hereby corrected as shown below:

Col. 2, line 36, "$n_6$" should read --$n_5$--.

Col. 4, line 44, "1,083" should read --1.083--.

Signed and Sealed this

Twenty-fifth Day of April, 1995

Attest:

BRUCE LEHMAN

*Attesting Officer*  *Commissioner of Patents and Trademarks*